United States Patent
Sijben et al.

(10) Patent No.: US 9,427,445 B2
(45) Date of Patent: Aug. 30, 2016

(54) METHOD FOR REDUCING THE OCCURRENCE OF INFECTION IN YOUNG CHILDREN

(75) Inventors: Johannes Wilhelmus Christina Sijben, Wageningen (NL); Martine Sandra Alles, Apeldoorn (NL)

(73) Assignee: N.V. Nutricia, Zoetermeer (NL)

(*) Notice: Subject to any disclaimer, the term of this patent is extended or adjusted under 35 U.S.C. 154(b) by 129 days.

(21) Appl. No.: 14/127,897

(22) PCT Filed: Jun. 22, 2012

(86) PCT No.: PCT/NL2012/050442
§ 371 (c)(1),
(2), (4) Date: Mar. 28, 2014

(87) PCT Pub. No.: WO2012/177135
PCT Pub. Date: Dec. 27, 2012

(65) Prior Publication Data
US 2014/0200195 A1  Jul. 17, 2014

(30) Foreign Application Priority Data

Jun. 22, 2011  (WO) ............... PCT/NL2011/050449

(51) Int. Cl.
| | |
|---|---|
| *A61K 31/702* | (2006.01) |
| *A61K 31/202* | (2006.01) |
| *A61K 31/592* | (2006.01) |
| *A61K 31/593* | (2006.01) |
| *A23L 1/29* | (2006.01) |
| *A23L 1/30* | (2006.01) |
| *A23L 1/308* | (2006.01) |
| *A61K 31/733* | (2006.01) |
| *A61K 31/715* | (2006.01) |
| *A61K 9/00* | (2006.01) |

(52) U.S. Cl.
CPC ............. *A61K 31/702* (2013.01); *A23L 1/296* (2013.01); *A23L 1/30* (2013.01); *A23L 1/3008* (2013.01); *A23L 1/3081* (2013.01); *A61K 9/0095* (2013.01); *A61K 31/202* (2013.01); *A61K 31/592* (2013.01); *A61K 31/593* (2013.01); *A61K 31/715* (2013.01); *A61K 31/733* (2013.01); *A23V 2002/00* (2013.01)

(58) Field of Classification Search
CPC ............. A61K 31/702; A61K 31/202; A61K 31/592; A61K 31/593; A61K 2300/00; A23L 1/296; A23L 1/3008; A23V 2002/00; A23V 2200/324; A23V 2250/0644
USPC .......................................................... 514/54
See application file for complete search history.

(56) References Cited

FOREIGN PATENT DOCUMENTS

| | | |
|---|---|---|
| EP | 1 714 564 A1 | 10/2006 |
| WO | WO-2005/122791 A2 | 12/2005 |
| WO | WO-2006/022542 A1 | 3/2006 |
| WO | WO-2006/022543 A1 | 3/2006 |
| WO | WO-2006/112716 A2 | 10/2006 |
| WO | WO-2006/112717 A2 | 10/2006 |
| WO | WO-2006/115412 A2 | 11/2006 |
| WO | WO-2007/105945 A2 | 9/2007 |
| WO | WO-2008/054192 A1 | 5/2008 |

OTHER PUBLICATIONS

Glossary of medical education terms, Institute of International Medical Education. http://www.iime.org/glossary.htm Accessed in Mar. 2013.*
Rijkers et al. Nutrition, The Infant and the Immune System. Dietary Components and Immune Function, Edited by: R.R. Watson et al.. DOI 10.1007/978-1-60761-061-8_1, pp. 3-23, 2010.*
Huth, Karl and Kluthe, Reinhold, "Lehrbuch der Ernahrungstherapie", Georg Thieme Verlag Stuttgart, New York, 1986.
International Search Report of PCT/NL2012/050442, mailed Dec. 3, 2012.

* cited by examiner

*Primary Examiner* — Clinton Brooks
*Assistant Examiner* — Yih-Horng Shiao
(74) *Attorney, Agent, or Firm* — Foley & Lardner LLP; Sunit Talapatra

(57) ABSTRACT

The invention pertains to the use of a composition in reducing the number of infections episodes and the occurrence of infections in young children, said composition comprising: (a) long chain polyunsaturated fatty acids, wherein the amount of arachidonic acid is less than 0.06 gram per 100 gram fatty acid; and comprising, per 100 g fatty acids: (i) 0.3-0.6 gram docosahexaenoic acid; (ii) 0.2-0.4 gram eicosapentaenoic acid; and (b) between 1.5 and 2.5 gram indigestible oligosaccharides per 100 kcal, comprising: (i) 1.4-2 gram short-chain galactooligosaccharides; and (ii) 0.1-0.5 gram long-chain fructopolysaccharides.

10 Claims, 2 Drawing Sheets

METHOD FOR REDUCING THE OCCURRENCE OF INFECTION IN YOUNG CHILDREN

CROSS-REFERENCE TO RELATED APPLICATION(S)

This application is the National Phase of International Patent Application No. PCT/NL2012/050443, filed Jun. 22, 2012, published as WO 2012/177135, which claims to priority to International Application No. PCT/NL2011/050449, filed Jun. 22, 2011. The contents of these applications are herein incorporated by reference in their entirety.

The invention is in the field of reducing the occurrence of infection in young children and/or reducing the number of infectious episodes in young children.

BACKGROUND DESCRIPTION

Blood levels of docosahexaenoic acid (DHA) and arachidonic acid (ARA) are typically higher in breast-fed infants than in infants fed formulas not containing these fatty acids. For these reasons, infant formula manufacturers and consumers are interested in providing DHA and ARA directly to infants. According to standing recommendations, infant formula should be supplemented with ARA in amounts at least equal to the amounts of DHA.

WO 2005/122790 discloses a composition comprising oligosaccharides and long-chain polyunsaturated fatty acids (LC-PUFAs) for improving intestinal barrier integrity. The LC-PUFAs involve a combination of DHA, eicosapentaenoic acid (EPA) and ARA, wherein ARA was found to be particularly effective in reducing tight junction permeability, and its thus favored in relatively high amounts, preferably at least 0.1 wt % ARA of the total fat.

WO 2006/022543 discloses a combination of oligosaccharides and immunoglobulins to treat infections. The combination may be incorporated into an infant formula further comprising LC-PUFAs, wherein it is believed that ARA, DHA and EPA act synergistically with the oligosaccharides. High amounts of ARA are advocated. WO 2006/115412 teaches similarly.

Outside the field, EP 1 714 564 and WO 2008/054192 relate to dust mite induced respiratory insufficiency and dust mite allergy, and visceral adiposity, respectively. To that end, both generally describe 0.1-5 wt % LC-PUFAs with 20 and 22 carbon atoms, based on total fat content, but their actual disclosures involve studies in which a treatment group received significant amounts of ARA, and infant nutrition recipes with only 0.25-0.27 wt %, based on lipid content, of DHA and EPA.

SUMMARY OF THE INVENTION

The inventors have observed in a clinical study with young children that by administering a specific formula the number of infections episodes and the occurrence of infections in young children are significantly reduced. A summary of the study is set out in Example 1 (including FIGS. 1 and 2). The percentage of young children that suffered from infectious episodes decreased significantly when administered a formula enriched with specific oligosaccharides and a LCPUFA composition comprising insignificant amounts of ARA. A second clinical study with infants as described in Example 2 confirmed that these lower ARA levels do not compromise the n3 LCPUFA (e.g., DHA and EPA) serum levels. In fact, it was found that excellent DHA and EPA serum values were yielded when administering the infants with low amounts of ARA but significant amounts of DHA and EPA. Details are provided further below.

In view of the art in the field, it is surprising that these results are obtained in young children. For example, many benefits have been ascribed to compositions comprising ARA in the art. However, the present composition has a low ARA content. The studies also evidence that significant amounts of n3 LCPUFAs (e.g., DHA and EPA) are required, in order to reduce the occurrence of infections and achieve satisfactory serum LCPUFA levels.

Additionally, it is surprising that the benefits were observed in a subpopulation which already consumes a variety of foodstuff, and only a relatively small part of the diets being provided by the described compositions (growing up milks) with present constitutes and amounts. It is particularly difficult to predict the effect of mixture of ingredients in young children.

DETAILED DESCRIPTION OF THE INVENTION

Figure 1:
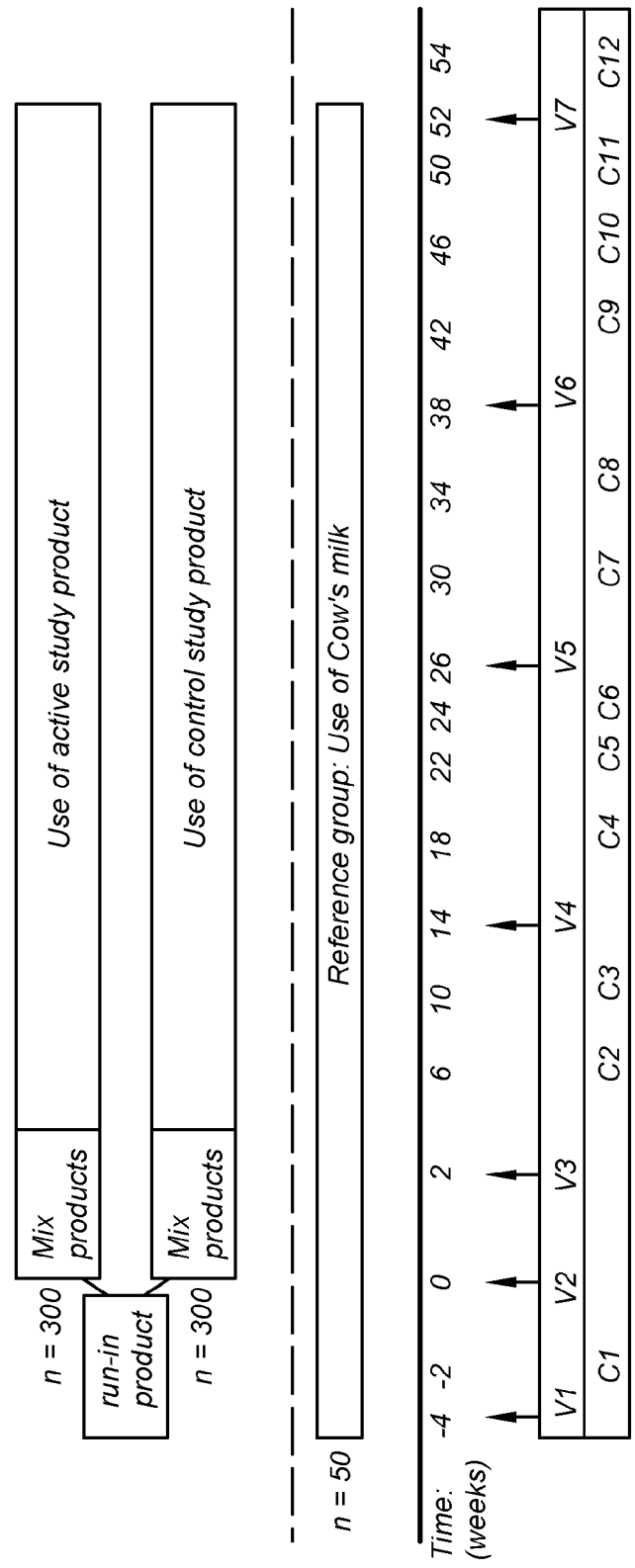
FIG. 1 provides a schematic of the study design for Example 1.

The present invention relates to a pharmaceutical or nutritional composition for use in the treatment and/or prevention of infections in young children; reducing the occurrence of infection in young children and/or reducing the number of infectious episodes in young children, said composition comprising:
a) long chain polyunsaturated fatty acids (LC-PUFAs) with 20 and 22 carbon atoms, wherein the amount of arachidonic acid (ARA) is less than 0.06 gram per 100 gram fatty acid; and comprising:
   (i) 0.3-0.6 gram docosahexaenoic acid (DHA, n-3) per 100 g fatty acids; and
   (ii) 0.2-0.4 gram eicosapentaenoic acid (EPA, n-3) per 100 g fatty acids; and
b1) between 1.5 and 2.5 gram indigestible oligosaccharides per 100 kcal, comprising:
   (i) 1.4-2 gram galactooligosaccharides with a degree of polymerization of 2-7; and
   (ii) 0.1-0.5 gram fructopolysaccharides with degree of polymerization of 2-150; or
b2) between 4 and 8 gram indigestible oligosaccharides per daily amount, comprising, per day:
   i) 3.7-6.4 gram galactooligosaccharides with a degree of polymerization of 2-7; and
   ii) 0.3-1.6 gram fructopolysaccharides with degree of polymerization of 2-150.

Worded differently, the present invention provides a method for the treatment and/or prevention of infections; reducing the occurrence of infection; and/or reducing the number of infectious episodes, by administering the composition as characterized herein to a young child.

The invention also pertains to the use of a composition characterized herein in the manufacture of a (pharmaceutical or nutritional) composition for the treatment and/or prevention of infections in young children; reducing the occurrence of infection; and/or reducing the number of infectious episodes in young children.

Polyunsaturated Fatty Acids

The present inventors surprisingly found that n3-LCPU-FAs, particularly eicosapentaenoic acid (EPA, 20:5 n-3) and docosahexaenoic acid (DHA, 22:6 n-3), most particularly DHA, in the absence/significantly low/very limited amount of ARA, and in combination with the specified oligosaccharides effectively aids in reducing the occurrence and severity of infections and the number of infectious episodes.

The present inventors found that lower concentrations of LC-PUFAs were effective in reducing the occurrence and severity of infections. Hence, the content of LCPUFA with 20 and 22 carbon atoms in the present composition, preferably does not exceed 2.0 wt % of the total fat content, more preferably does not exceed 1.5 wt %, even more preferably does not exceed 1.4 wt %, most preferably does not exceed 1.2 wt % of the total fat content. LCPUFA as used in the present invention refers to polyunsaturated fatty acids with a 20 or 22 carbon chain. Preferably the present composition comprises at least 0.50 wt %, preferably at least 0.60 wt %, more preferably at least 0.70 wt % LC-PUFAs with 20 and 22 carbon atoms of the total fat content.

The EPA content preferably ranges between 0.25 and 0.35 wt % of the fatty acids, more preferably does not exceed 0.30 wt % of the fatty acids. The DHA content preferably ranges between 0.35 and 0.55 wt %, more preferably does not exceed 0.50 wt % of the fatty acids.

It is preferred that at least 80 wt %, more preferably at least 85 wt %, most preferably 85-100 wt % of the LCPU-FAs with 20 and 22 carbon atoms is provided by the combination of EPA and DHA.

However, while the art promotes the use of significant amounts of ARA in infant formulae, it was found by the present inventors that excellent results are obtained when ARA levels are in fact low, preferably lower than 0.05 wt % of total fat. It is preferred that the composition comprises relatively low amounts, preferably less than 0.04 wt % of the total fat. The amount of ARA is preferably between 0 and 0.05 wt. %, more preferably between 0.01 and 0.05 wt. %.

If ARA is present, the weight ratio ARA:DHA preferably is below 0.2, more preferably below 0.15, most preferably below 0.10. If ARA is present, the weight ratio ARA:EPA is preferably less than 0.8, more preferably less than 0.5, most preferably less than 0.2. The weight ratio DHA:EPA is preferably in the range of 1:1 to 2:1, preferably about 3:2. It is noted that this is merely an approximate limit.

The docosapentaenoic acid (DPA) content preferably ranges between 0.01 and 0.20 wt % of the total fatty acids. Preferably, the present composition comprises 0.01-0.15 gram docosapentaenoic acid (DPA, 22:5 n-3) per 100 g fatty acids.

It is preferred that the omega-6 LC-PUFA:omega-3 LC-PUFA weight ratio is between 1:1 and 7:1, more preferably between 2:1 and 6:1, most preferably between 3:1 and 5:1, most preferably less than 5:1, in particular less than 4.8:1.

The present composition preferably comprises between 5 and 75 wt % polyunsaturated fatty acids based on total fat, preferably between 10 and 50 wt %, most preferably between 10 and 25 wt %.

The LC-PUFAs with 20 and 22 carbon atoms may be provided as free fatty acids, in triglyceride form, in phospholipid form, or as a mixture of one of more of the above. The present composition preferably comprises at least one of EPA and DHA, more preferably at least DHA, in triglyceride form. Preferably the present composition contains fish oil.

The present nutritional composition preferably also provides omega-9 (n-9) fatty acid (preferably oleic acid, 18:1), to provide sufficient nutrition. Preferably the present composition provides at least 15 wt % n-9 fatty acid based on the weight of the total fatty acids, more preferably at least 25 wt %. The content of n-9 fatty acids is preferably below 80 wt %.

It is preferred to maintain weight ratios of stearidonic acid (18:4) to DHA and to EPA below 0.1.

Oligosaccharides

The composition preferably comprises between 1.5 and 2.5 gram indigestible oligosaccharides per 100 kcal, comprising:
  i) 1.4-2 gram galactooligosaccharides with a degree of polymerization of 2-7; and
  ii) 0.1-0.5 gram fructopolysaccharides with degree of polymerization of 2-150.

In one embodiment, the composition preferably comprises a daily amount between 4 and 8 gram, preferably 5-7 gram indigestible oligosaccharides per daily amount, comprising, per day:
  i) 3.7-6.4 gram, preferably 4.5-5.6 gram galactooligosaccharides with a degree of polymerization of 2-7; and
  ii) 0.3-1.6 gram, preferably 0.5-1.4 gram fructopolysaccharides with degree of polymerization of 2-150.

The term "fructopolysaccharides" comprises fructans and inulin, and hydrolyzates thereof, and is regarded interchangeably with the term "fructooligosaccharides". The preferred galactooligosaccharides are transgalactooligosaccharides.

It is preferred that at least 95 wt %, preferably 95-100 wt % of the indigestible oligosaccharides is provided by galactooligosaccharides and fructopolysaccharides.

In a particularly preferred embodiment the present composition comprises transgalacto-oligosaccharide. Transgalacto-oligosaccharide can be defined as $[galactose]_n$-glucose and/or $[galactose]_n$-glucose-[galactose] wherein n is an integer from 1 up to and including 7. Preferably the present composition comprises $[galactose]_n$-glucose wherein n is an integer from 1 up to and including 6. This type of galactooligosaccharides is sometimes referred to as scGOS.

The term "fructo-polysaccharide" as used herein preferably refers to a non-digestible polysaccharide carbohydrate comprising a chain of at least 2β-linked fructose units, with a degree of polymerization (DP) of 2 to 250, preferably 7 to 100, more preferably 20 to 60. Preferably inulin is used. Inulin is available under the tradename "Raftilin HP®" (Orafti). The average DP of the present fructopolysaccharide is preferably at least 7, more preferably at least 10, preferably below 100, most preferably between 10 and 30, most preferably between 20 and 23. Fructopolysaccharide with an average DP between 10 and 30 is sometimes referred to as lcFOS. The fructopolysaccharide used preferably has the (majority of) fructose units linked with a β(2→1) linkage. Other terms for fructopolysaccharides include inulin, fructooligosaccharide, polyfructose, fructans and oligofructose. The present composition preferably comprises fructopoly/oligosaccharides with a DP of 2 to 100.

Formula

The composition is preferably administered orally.

The present composition preferably includes protein, carbohydrate and fat. It is preferably administered in liquid form. The term "liquid food" as used in the present invention includes dry food (e.g. powders) which are accompanied with instructions as to admix said dry food mixture with a suitable liquid (e.g. water).

The present composition is preferably provided as a packaged powder or packaged ready-to-feed formula. To prevent spoilage of the product, packaging size of ready-to-feed formula preferably does not exceed one serving, e.g.

preferably does not exceed 1500 ml; and packaging size of the present composition in powder form preferably does not exceed 250 servings. Suitable packaging sizes for the powder are 2000 grams or less, preferably per 1000 grams or less.

Because lactose is an important carbohydrate source for young children, the present composition preferably comprises at least 35 wt % lactose based on weight of total digestible carbohydrate, more preferably at least 50 wt %, most preferably at least 75 wt %. Preferably, the composition comprises at least 1 g lactose/100 ml, more preferably at least 2 g/100 ml, even more preferably at least 5 g per 100 ml. The present composition preferably comprises 4 g to 18 g, more preferably 4 to 14 g digestible carbohydrates per 100 ml composition.

Preferably, the composition comprises 4 to 20 en % protein, 20 to 50 en % fat, and 25 to 85 en % carbohydrates. More preferably, the composition comprises 8 to 10 en % protein, 35 to 45 en % fat, and 45 to 55 en % carbohydrates. "En %" is short for energy percentage and represents the relative amount each constituent contributes to the total caloric value of the preparation. The caloric value is provided by digestible carbohydrates, protein and fat. The protein may comprise a member selected form the group consisting of hydrolyzed milk protein, vegetable protein and/or amino acids.

In a preferred embodiment, the composition comprises vitamin D. Vitamin D is a group of fat-soluble secosteroids. There are two major physiologically relevant forms which are vitamin D2 (ergocalciferol) and vitamin D3 (cholecalciferol). These are known collectively as calciferol. In the context of the invention, the term 'vitamin D' refers to all forms of vitamin D, either D1, D2, D3, or D4, in particular D2 and D3, or any mixture thereof. Excellent results are obtained with inclusion of vitamin D for immunity and infection, Vitamin D may be provided in an active (1,25 $(OH)_2D$) or inactive (Vit D3 or D2) form.

The packaged products preferably provided with labels that explicitly or implicitly direct the consumer towards the use of said product in accordance with one or more of the above or below purposes, are encompassed by the present invention. Such labels may for example make reference to the present method by including wording like "reduced infection", "reduced infectious episodes", "protects your child", "defense against bacteria and viruses", or similar wording, in accordance with the findings of the clinical study.

In one embodiment, the composition is preferably a nutritional or dietary supplement suited for the targeted infant population, thus disclaiming infant (milk) nutrition.

The present composition is preferably prepared by admixing a powdered composition comprising with water. The present invention thus also relates to a packaged power composition wherein said package is provided with instructions to admix the powder with a suitable amount of liquid.

In one preferred embodiment, the present composition is administered to a young child, wherein the above-mentioned oligosaccharides are administered in a dosage of 0.8-1.6 g/100 ml, preferably 1.0-1.4 g/100 ml, and wherein said n-3 LCPUFAs are administered in a dosage of 15-25 mg/100 ml, preferably 18-22 mg/100 ml.

In one preferred embodiment, the present composition is administered to a young child, wherein the above-mentioned oligosaccharides are administered in a daily dosage of 4-8 g, preferably 4.5-7.5 g, more preferably 5-7 g, and wherein said n-3 LCPUFAs are administered in a daily dosage of 60-130 mg, preferably 70-120 mg, more preferably 80-110 mg.

Preferably the present composition is administered in liquid form to a young child in a daily amount of 250-750 ml, more preferably 400-750 ml per day, more preferably 400-600 ml per day, optimally about 500 ml per day. It is preferred that the daily dosage of the indigestible oligosaccharides (preferably GOS and fructopolysaccharides) is at least 3.5 gram and the daily dosage of n-3 LCPUFAs is at least 55 mg. It is however preferred that the oligosaccharides and the n-3 LCPUFAs are administered in a daily dosage of about 5.0-7.0 g and 80-110 mg, respectively. The recommended daily amounts are about 6.0 and 100 mg for the oligosaccharides and the n-3 LCPUFAs, respectively. It is noted that these recommended values are merely approximate limits. In this paragraph, "the oligosaccharides" is to be understood as the combination of (i) short-chain galactooligosaccharides and (ii) long-chain fructopolysaccharides here above. The term "n-3 LCPUFAs" in this paragraph refers to the combination of DHA and EPA.

According to one embodiment, vitamin D is administered in an amount of 200-800 μg per daily dosage, preferably 300-700 μg, more preferably 400-600 μg per daily dosage. According to one embodiment, vitamin D is used in an amount of 40-160 μg per 100 ml, preferably 60-140 μg, more preferably 80-120 μg per 100 ml. The above numbers can be converted into IU if deemed appropriate.

Preferably the present composition is administered to the young child at least twice per week, more preferably at least 5 times per week, more preferably daily. Preferably the composition is administered for at least 10 consecutive weeks, preferably at least 26 consecutive weeks, more preferably at least 50 consecutive weeks.

Infections

The present invention relates to the use of the present composition in young children with the age between 10 and 48 months, preferably between 10 and 36 months, more preferably with the age between 11 and 40 months, more preferably from 1 year to 3 years. Preferably the young children are healthy children, preferably young children not diagnosed with an illness or disease.

The present invention preferably relates to intestinal and/or respiratory tract infections. Both the respiratory and intestinal tract are common sites for infection by pathogens. In one embodiment, the invention preferably relates to reducing the incidence of respiratory tract infections. In another embodiment, the invention preferably relates to reducing the incidence of intestinal infections. The present composition is preferably administered to young children attending daycare centers. These children are exposed to a plurality of microorganisms that can cause infections.

The present invention also provides for a packaged liquid or powder composition providing per 100 ml liquid composition or 100 ml in water reconstituted powder composition:

a. 15-25 mg long chain polyunsaturated fatty acids (LCPUFAs) with 20 and 22 carbon atoms, wherein the amount of arachidonic acid (ARA) is less than 0.06 gram per 100 gram fatty acids; and comprising:
   (i) 0.3-0.6 gram docosahexaenoic acid (DHA, n-3) per 100 g fatty acids; and
   (ii) 0.2-0.4 gram eicosapentaenoic acid (EPA, n-3) per 100 g fatty acids; and
b. 1-1.5 gram indigestible oligosaccharides per 100 ml, and between 1.5 and 2.5 gram indigestible oligosaccharides per 100 kcal, comprising:

(i) 1.4-2 gram per 100 kcal galactooligosaccharides with a degree of polymerization of 2-7; and (ii) 0.1-0.5 gram per 100 kcal fructopolysaccharides with degree of polymerization of 2-150, and an average degree of polymerization between 10 and 30.

In one embodiment, the present invention also provides for a packaged liquid or powder composition providing per daily dosage:

a) 60-130, preferably 70-120 mg, more preferably 80-110 mg long chain polyunsaturated fatty acids (LC-PUFAs) with 20 and 22 carbon atoms, wherein the amount of arachidonic acid (ARA) is less than 0.06 gram per 100 gram fatty acids; and comprising:

(i) 0.3-0.6 gram docosahexaenoic acid (DHA, n-3) per 100 g fatty acids; and (ii) 0.2-0.4 gram eicosapentaenoic acid (EPA, n-3) per 100 g fatty acids; and b) 4-8 gram, preferably 5-7 gram indigestible oligosaccharides per day, comprising, per day:

(i) 3.7-6.4 gram, preferably 4.5-5.6 gram galactooligosaccharides with a degree of polymerization of 2-7; and (ii) 0.3-1.6 gram, 0.5-1.4 gram fructopolysaccharides with degree of polymerization of 2-150, and an average degree of polymerization between 10 and 30.

The composition preferably comprises 4 to 20 en % protein, 20 to 50 en % fat, and 25 to 85 en % carbohydrates. More preferably, the composition comprises 8 to 10 en % protein, 35 to 45 en % fat, and 45 to 55 en % carbohydrates.

In one embodiment, the packaged liquid or powder composition further comprises vitamin D, preferably in the forms and amounts indicated above.

Example 1

Clinical Study on the Incidence of Infections

The study objective was to investigate the effect of the composition of the invention on the occurrence of infections in children attending daycare centers, age 1-3 years. The study design is shown in FIG. 1, the statistics given in Table 1.

The compositions of the control and the 'invention diet' are listed in Table 2 (Table 2A showing the fatty acid compositions). The invention diet had a total saturated fatty acids content of 25.2% (of all fatty acids); an omega-6:omega-3 weight ratio of 4.1:1; and a LA:ALA weight ratio of 5.4:1. The numbers for the control diet were 24.9%, 5.5:1 and 5.4:1, respectively.

TABLE 1

Number of participants in study

| | |
|---|---|
| Screened | 907 |
| Randomized | 768 |
| Reference group | 37 |
| SF at V2 | 103 |
| Drop out after V2 | 73 |
| Completed | 731 |

TABLE 2

Ingredients [per 100 kg powder]

| INGREDIENTS | CONTROL | Invention diet |
|---|---|---|
| Demineralized whey [kg] | 21.0 | 19.4 |
| Vegetable oils [kg] | 21.2 | 19.1 |
| Skimmed milk [kg] | 17.7 | 16.3 |
| Maltodextrin [kg] | 17.3 | 13.5 |
| Dietary fibers [kg]: | — | 12.7 |
| galactooligosaccharides [kg] | — | 11.9 |
| fructopolysaccharides [kg] | — | 0.798 |
| Lactose [kg] | 16.6 | 12.6 |
| Whey protein concentrate [kg] | 3.97 | 3.58 |
| Tricalcium phosphate [kg] | 0.460 | 0.398 |
| Fish oil [kg] | — | 0.384 |
| Calcium carbonate [kg] | 0.366 | 0.356 |
| Tri potassium citrate [kg] | 0.288 | 0.257 |
| Tri sodium citrate [kg] | 0.125 | 0.140 |
| L-ascorbic acid [g] | 95.1 | 87.4 |
| Magnesium chloride[g] | 79.7 | 66.8 |
| Soy lecithin[g] | 37.8 | 59.5 |
| Taurine[g] | 36.7 | 34.1 |
| Choline chloride[g] | 34.2 | 30.1 |
| Vanillin[g] | 32.5 | 30.0 |
| Sodium L-ascorbate[g] | 32.5 | 29.9 |
| Ferrous sulphate[g] | 25.9 | 23.8 |
| Potassium chloride[g] | 21.5 | 23.0 |
| Zinc sulphate[g] | 15.4 | 13.9 |
| DL-alpha tocopheryl acetate[g] | 3.89 | 3.62 |
| Nicotinamide[g] | 3.13 | 2.87 |
| Folic acid[g] | 1.32 | 1.21 |
| Cholecalciferol[g] | 1.30 | 1.19 |
| Calcium D-pantothenate[g] | 1.24 | 1.08 |
| Cupric sulphate[g] | 1.16 | 1.07 |
| Retinyl palmitate[g] | 0.959 | 0.879 |
| DL-alpha tocopherol[g] | 0.913 | 0.836 |
| D-biotin[g] | 0.694 | 0.638 |
| Retinyl acetate[g] | 0.661 | 0.627 |
| Thiamin hydrochloride[g] | 0.436 | 0.402 |
| Cyanocobalamin[g] | 0.251 | 0.325 |
| Pyridoxine hydrochloride[g] | 0.246 | 0.245 |
| Riboflavin[g] | 0.206 | 0.226 |
| Potassium iodide[mg] | 87.4 | 67.0 |
| Manganese sulphate[mg] | 75.6 | 54.6 |
| Phytomenadione[mg] | 29.9 | 27.4 |
| Sodium selenite[mg] | 21.9 | 20.3 |

TABLE 2A

Fatty acid composition for Example 1*

| | CONTROL | | Invention diet | |
|---|---|---|---|---|
| | Per 100 g fatty acids | Per 100 g powder | Per 100 g fatty acids | Per 100 g powder |
| C16:0 palmitic acid | 19.2 | 3.96 | 19.2 | 3.62 |
| C18:0 stearic acid | 3.48 | 0.72 | 3.50 | 0.66 |
| C18:1 oleic acid | 57.3 | 11.8 | 56.3 | 10.7 |
| C18:2 linoleic acid | 14.2 | 2.93 | 14.0 | 2.65 |
| C18:3 alpha-linolenic acid | 2.64 | 0.542 | 2.60 | 0.492 |
| C20:0 arachidic acid | 0.42 | 0.09 | 0.42 | 0.08 |
| C20:1 eicosaenoic acid | 0.55 | 0.11 | 0.268 | 0.051 |
| C20:4 arachidonic acid | — | — | 0.034 | 0.006 |
| C20:5 eicosapentaenoic acid | — | — | 0.268 | 0.051 |
| C22:0 behenic acid | 0.44 | 0.09 | 0.44 | 0.08 |
| C22:1 erucic acid | 0.11 | 0.02 | 0.11 | 0.02 |
| C22:5 docosapentaenoic acid | — | — | 0.06 | 0.01 |
| C22:6 docosahexaenoic acid | — | — | 0.402 | 0.076 |

*The list of fatty acids is not exhaustive. Listed are those present in significant amounts and considered relevant for the purpose of the study.

In a randomized, double-blind, controlled, parallel, multi-country intervention trial, 767 healthy children, aged 11-29 months, received the 'invention diet' with scGOS/lcFOS/LCPUFA, or 'control diet' (without scGOS/lcFOS/LCPUFA) for 52 weeks.

For the invention diet, the aimed daily intake was at least 6.0 g of scGOS/lcFOS and 100 mg of n-3 LCPUFA (DHA and EPA) in 500 ml. The composition included 1.2 g/100 ml of scGOS/lcFOS (about 9:1 weight ratio) and 19.2 mg/100 ml of n-3 LCPUFA (DHA and EPA).

Parents completed a daily diary on occurring illness symptoms (not distinguishing between upper respiratory tract infections and gastrointestinal infections).
A Zero-inflated Negative—Binomial regression Model was used that combines two separate parts: a binomial part (a subject would get an infection: yes/no) and a negative-binomial part fitting the counts for infections for the subjects.
Results Children in the 'invention diet' group compared with the control group had a decreased risk of having at least one infection (299/388 (77%) vs. 313/379 (83%), respectively, RR=0.93, 95% CI 0.87-1; chi-square p=0.057; logistic regression p=0.0259).

Figure 2:
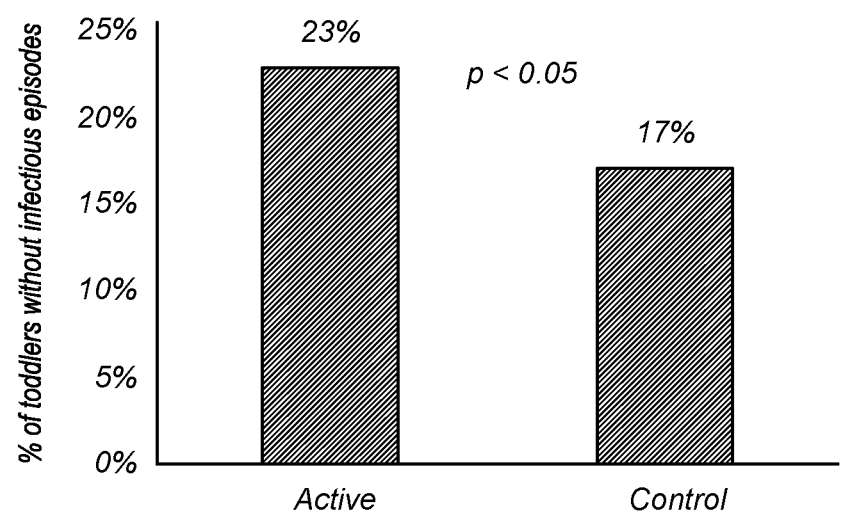
FIG. 2 is a graph showing the percentage of toddlers receiving an "active" or "control" diet that did not have any infectious episodes.

In other words, the results show a trend toward a significant effect on number of infectious episodes (p=0.0743). This trend is driven by a significant increased chance of having no infectious episode, as shown in FIG. 2, in terms of the percentage of young children that were not reported to have suffered from infectious episodes (p<0.05).

Example 2

Clinical Study on LCPUFA Serum Levels

The aim of this study was to measure the effect of a supplement with scGOS/lcFOS (about 9:1 weight ratio) and n-3 LCPUFA in healthy children.

In this double-blind, placebo-controlled study, 195 children aged 1-3 years were randomized to receive a composition with scGOS/lcFOS and 16.9 mg/100 mL n-3 LCPUFA (Group 1), a composition with scGOS/lcFOS and 1.3 mg/100 mL n-3 LCPUFA (Group 2) or a composition with no scGOS/lcFOS and 1.3 mg/100 mL n-3 LCPUFA (Group 3) for 12 weeks. Mean daily intake was about 540 ml of said compositions.

Table 3 shows the fatty acid content of the compositions.

TABLE 3

Fatty acid composition for Example 2*

| | Groups 2 and 3 | | Group 1 | |
|---|---|---|---|---|
| | Per 100 g fatty acids | Per 100 g powder | Per 100 g fatty acids | Per 100 g powder |
| C16:0 palmitic acid | 19.5 | 2.09 | 19.4 | 2.01 |
| C18:0 stearic acid | 3.43 | 0.37 | 3.44 | 0.36 |
| C18:1 oleic acid | 54.9 | 5.88 | 54.0 | 5.58 |
| C18:2 linoleic acid | 14.4 | 1.54 | 14.1 | 1.46 |
| C18:3 alpha-linolenic acid | 2.53 | 0.271 | 2.49 | 0.258 |
| C20:0 arachidic acid | 0.41 | 0.04 | 0.41 | 0.04 |
| C20:1 eicosaenoic acid | 0.51 | 0.11 | 0.53 | 0.06 |
| C20:4 arachidonic acid | 0.108 | 0.012 | 0.04 | 0.004 |
| C20:5 eicosapentaenoic acid | 0.011 | 0.001 | 0.305 | 0.032 |
| C22:0 behenic acid | 0.44 | 0.05 | 0.43 | 0.04 |
| C22:1 erucic acid | 0.11 | 0.01 | 0.11 | 0.01 |
| C22:5 docosapentaenoic acid | — | — | 0.06 | 0.01 |
| C22:6 docosahexaenoic acid | 0.054 | 0.006 | 0.475 | 0.049 |

*The list of fatty acids is not exhaustive. Listed are those present in significant amounts and considered relevant for the purpose of the study.

Serum samples were obtained in 128 children at baseline and at week 12.

As shown in Table 3, ARA and n-3 LC-PUFA concentrations in the Group 1 supplement were about 0.04 g and 0.84 g per 100 g fatty acids, respectively, in accordance with those reported for the intervention diet of example 1 (i.e. 0.034 g and 0.73 g per 100 g, respectively). ARA and n-3 LC-PUFA concentrations in the Group 2 and 3 supplements were about 0.108 g and 0.065 g per 100 g fatty acids. In groups 1 and 3, scGOS/lcFOS levels were similar to those in example 1, i.e. aimed daily intake of at least 6.0 g of scGOS/lcFOS.
Results There were no differences in the baseline characteristics between study groups. Mean intake of the composition was similar in all groups during the study (range 530-542 mL/day). Between baseline and week 12, there was a significant increase in serum DHA (46.0-53.7 mg/L, p<0.001) and EPA (7.0-8.6 mg/L, p=0.001) in Group 1, while significant decrease in serum DHA and EPA in both Group 2 (45.6-40.0 mg/L and 7.2-4.6 mg/L, respectively, both p<0.001) and Group 3 (45.4-39.0 mg/L, p<0.001 and 7.1-5.4 mg/L, p=0.007, respectively). These changes were significantly different in Group 1 compared to Group 3, and to Group 2 (both p<0.001) but not different when compared Group 2 to Group 3 (p=0.858).

The decrease of serum DHA and EPA observed in Group 2 and Group 3 (with 1.3 mg/100 mL DHA+EPA) over the 12 weeks period indicates that depletion of n-3 LCPUFA may occur. Therefore, infant nutrition with adequately high n-3 LCPUFA levels (including low amounts of ARA) can help to improve the n-3 LCPUFA status in young children aged 1-3.

The invention claimed is:

1. A method for reducing occurrence of respiratory tract or intestinal infection in young children, reducing number of infectious episodes in respiratory tract or intestine in young children, and/or treatment of respiratory tract or intestinal infections in young children, the method comprising administering to young children suffering from respiratory tract infections a composition comprising:
   (a) long chain polyunsaturated fatty acids (LC-PUFAs) with 20 and 22 carbon atoms, comprising less than 0.06 gram arachidonic acid (ARA) per 100 gram total fatty acid; and
      (i) 0.3-0.6 gram docosahexaenoic acid (DHA, n-3) per 100 g total fatty acids; and
      (ii) 0.2-0.4 gram eicosapentaenoic acid (EPA, n-3) per 100 g total fatty acids;
   wherein the weight ratio of ARA:DHA is below 0.1 and the weight ratio of ARA:EPA is below 0.2;
   and one of (b1) or (b2):
   (b1) between 1.5 and 2.5 gram per 100 kcal indigestible oligosaccharides, comprising:
      (i) 1.4-2 gram galactooligosaccharides with a degree of polymerization of 2-7; and
      (ii) 0.1-0.5 gram fructopolysaccharides with a degree of polymerization of 2-150; or
   (b2) a daily amount of between 4 and 8 gram indigestible oligosaccharides, comprising, per day:
      (i) 3.7-6.4 gram galactooligosaccharides with a degree of polymerization of 2-7; and
      (ii) 0.3-1.6 gram fructopolysaccharides with a degree of polymerization of 2-150.

2. The method according to claim 1, wherein at least 80 wt % of the LC-PUFAs is provided by a combination of EPA and DHA.

3. The method according to claim 1, wherein the composition comprising 0.01-0.2 gram docosapentaenoic acid (DPA, n-3) per 100 g total fatty acids.

4. The method according to claim 1, wherein the composition comprising 0.25-0.35 g EPA and 0.35-0.55 g DHA per 100 g total fatty acids.

5. The method according to claim 1, wherein at least 95 wt % of the indigestible oligosaccharides is provided by the galactooligosaccharides and fructopolysaccharides.

6. The method according to claim 1, wherein the composition comprising 8-10 en % protein, 45-55 en % carbohydrates and 35-45 en % fat; and has a caloric value of 0.5-0.75 kcal per 100 ml.

7. The method according to claim 1, wherein the composition has an omega-6 LC-PUFA:omega-3 LC-PUFA weight ratio other than ARA:DHA and ARA:EPA between 1:1 and 7:1.

8. The method according to claim 1, wherein the composition has a weight ratio of DHA:EPA in a range of 1:1 to 2:1.

9. The method according to claim 1, wherein the composition further comprises vitamin D.

10. The method according to claim 9, wherein the composition comprises vitamin D in a daily dosage of 200-800 µg.

* * * * *